US00PP31101P2

(12) United States Plant Patent
Delabroye

(10) Patent No.: US PP31,101 P2
(45) Date of Patent: Nov. 19, 2019

(54) ***HEUCHERA* PLANT NAMED 'MAPLE LEAF'**

(50) Latin Name: ***Heuchera* hybrid**
Varietal Denomination: Maple Leaf

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 0 days.

(21) Appl. No.: 16/350,618

(22) Filed: Dec. 11, 2018

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Heuchera* named 'Maple Leaf' that is characterized by its glossy young leaves, its flowers that are white in color and its unique foliage that is orange in color.

2 Drawing Sheets

Botanical classification: *Heuchera* hybrid.
Cultivar designation: 'Maple Leaf'.

CROSS REFERENCE TO RELATED APPLICATIONS

This application is related to U.S. Plant Patents for plants derived from the same breeding program that are entitled *Heuchera* Plant Named 'Vulcano' (U.S. Plant Pat. No. 25,625) and 'Apricot' (U.S. Plant Pat. No. 27,139).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Heuchera* of hybrid origin, botanically known as a *Heuchera* and is hereinafter referred to by its cultivar name 'Maple Leaf'.

The new cultivar was discovered as a chance seedling in a trial field by the Inventor in Hantay, France in April of 2016. The trial field contained hundreds of proprietary *Heuchera* seedlings from the Inventor's breeding program and other cultivars. The exact parentage of 'Maple Leaf' is therefore unknown.

Asexual propagation of the new cultivar was first accomplished under the direction of the Inventor by tissue culture initiated from meristem tissue in Rijswijk, The Netherlands in April 2017. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Maple Leaf' as a new and unique cultivar of *Heuchera*.

1. 'Maple Leaf' exhibits glossy young leaves.
2. 'Maple Leaf' exhibits flowers that are white in color.
3. 'Maple Leaf' exhibits unique foliage that is orange in color.

'Maple Leaf' can be most closely compared to the *Heuchera* cultivars 'Vulcano' and 'Apricot'. 'Vulcano' is similar to 'Maple Leaf' in foliage shape. 'Vulcano' differs from 'Maple Leaf' in having foliage that is lighter orange in color and young foliage with matte surfaces. 'Apricot' is similar to 'Maple Leaf' in foliage color. 'Apricot' differs from 'Maple Leaf' in having young foliage with matte surfaces, flowers that are pink color, a smaller plant size and a less vigorous plant habit.

BRIEF DESCRIPTION OF THE DRAWINGS

The accompanying colored photograph illustrates the overall appearance and distinct characteristics of the new *Heuchera*. The photograph was taken of a plant 18 months in age as grown in a polyethylene tunnel in a 27-cm container in Hantay, France.

The photograph in FIG. 1 provides a side view of the plant of 'Maple Leaf' in bloom.

Figure 1:
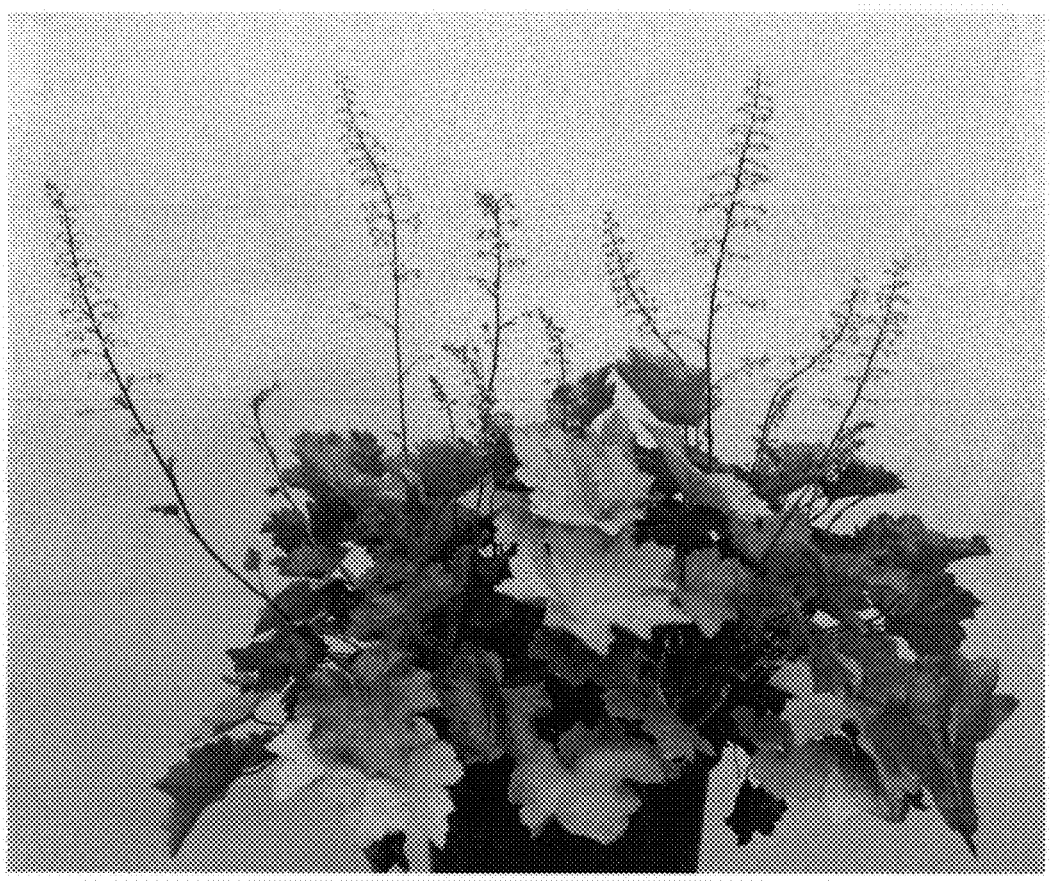
Figure 2:
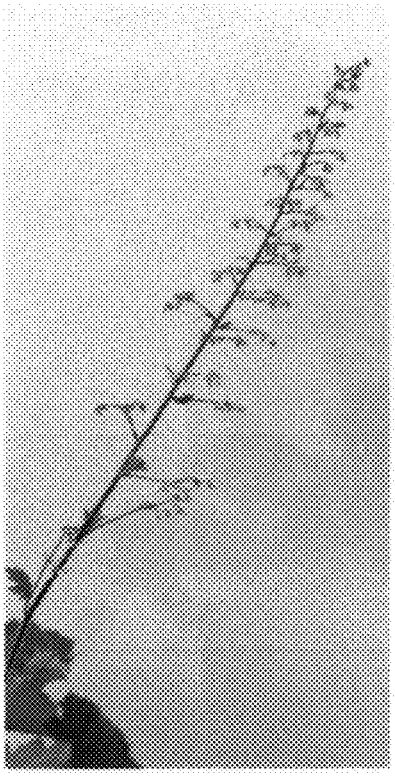

The photograph in FIG. 2 provides a close up of the inflorescence of 'Maple Leaf'.

Figure 3:
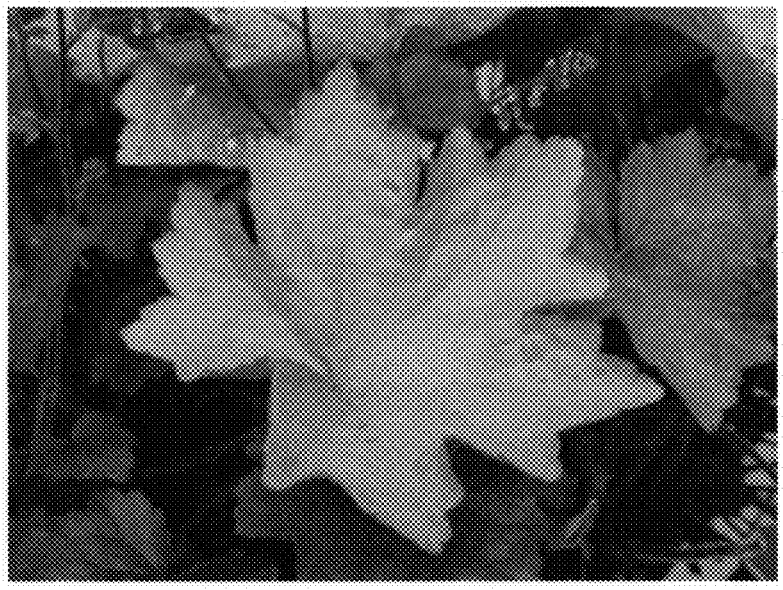

The photograph in FIG. 3 provides a close up of the foliage of 'Maple Leaf'.

The colors in the photograph are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown outdoors in 27-cm containers in Hantay, France. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—An average of 6 weeks in May and June in Hantay France.

*Plant type.*—Herbaceous perennial.

*Plant habit.*—Flattened globular with inflorescences held above the foliage.

*Height and spread.*—An average of 65 cm in height to top of foliage and 90 cm in width.

*Hardiness.*—At least in U.S.D.A. Zones 3 to 9.

*Diseases and pests.*—No susceptibility or resistance to diseases or pests has been observed.

*Root description.*—Fibrous roots on woody rootstalks, 158D in color.

*Propagation.*—Tissue culture.

*Root development.*—12 to 13 weeks to fully develop from a tissue culture plug in a 7-cm container.

*Growth rate.*—Moderate to high.

Stem description (peduncle, flowering stem):

*Shape.*—Round.

*Stem color.*—Young; N77B, mature and at internodes; N186C and 200D.

*Stem size.*—An average of 3 mm in diameter and 56 cm in length.

*Stem strength.*—Strong.

*Stem aspect.*—Average angle of 30° (0°=horizontal), secondary peduncle average of 70° (0°=horizontal).

*Stem surface.*—Glabrous.

*Stem number.*—Average of 12 flowering stems.

*Internode length.*—An average of 2 mm.

*Branching habit.*—Flowering stems emerge from basal rosette.

Foliage description:

*Leaf shape.*—Near orbicular.

*Leaf division.*—Simple.

*Leaf base.*—Hastate, lobes touching to slightly overlapping.

*Leaf apex.*—Short abruptly acute.

*Leaf venation.*—Laciniate, upper surface 198A, lower surface N187C.

*Leaf margins.*—Crenate with abruptly acute tips on each tooth.

*Leaf attachment.*—Petiolate.

*Leaf arrangement.*—Alternate in basal rosettes.

*Leaf lobes.*—Lobed, an average of 7 lobes, shallow in depth, divergent.

*Leaf surface.*—Both surfaces glossy, non-rugose and pubescent, moderately covered with very short strigose hairs an average of 0.5 mm in length and N155A in color.

*Leaf color.*—Young upper surface; N199B and N199C, young lower surface; 187D, mature upper surface; 177C, fading to 164B, mature lower surface; 183D.

*Leaf size.*—An average of 14.6 cm in length and 14.1 cm in width.

*Leaf quantity.*—An average of 12 per basal rosette.

*Petioles.*—An average of 20.4 cm in length and 4 mm in diameter, color upper and lower surface color 183B, both surfaces slightly glossy, moderate in strength, densely covered with soft hairs; an average of 1.5 mm in length and N155A in color.

*Stipules.*—Leafy stipule at the base of each leaf, in basal leaves average length 1.5 cm, average width 3 mm, tip acute, 183A in color.

Flower description:

*Inflorescence type.*—Numerous small bell-shaped flowers arranged on panicles on peduncles emerging from a basal rosette.

*Inflorescence size.*—An average of 29.2 cm in height and 6.9 cm in diameter.

*Inflorescence number.*—An average of 11.

*Flower fragrance.*—None.

*Flower quantity.*—Average of 250 flowers per flowering stem.

*Flower lastingness.*—Average of 10 days.

*Flower buds.*—Obovate in shape, an average of 2.5 mm in length and 1.5 mm in diameter, color; upper half 151D, lower half 200D, surface is matte and densely covered with very short glandular hairs; an average of 0.5 mm in length and N155A in color.

*Flower aspect.*—Nodding.

*Flower type.*—Single, campanulate.

*Flower size.*—Average of 2.5 mm in height and diameter, 6 mm in length.

*Petals.*—Average of 5, rotate arrangement and implanted in the hypanthium at base, oblanceolate in shape and curled, margin is entire, apex is acute, base is narrow attenuate, upper and lower surface is glabrous and smooth, color of upper and lower surface when opening and when fully open; NN155D, an average of 2 mm in length and 0.5 mm in width.

*Calyx.*—Campanulate, sepals fused to hypanthium, 3 mm in length and 2.5 mm in diameter.

*Sepals.*—An average of 5, lower 60% fused into campanulate hypanthium, oblong in shape, an average of 3 mm in length and 0.5 mm in width, margin is entire and fused into hypanthium, apex is obtuse, fused base, color; when opening upper and lower surface 151D, lower half 200D, fully open upper and lower surface 145D, lower half 145A, both surfaces are matte, lower surface is densely covered with very short glandular hairs an average of 0.5 mm in length and N155A in color.

*Pedicels.*—An average of 2.5 mm in length and 0.5 mm in diameter, 183A in color and fading at distal end to 145C, primary flower aspect straight on top of secondary pedicel, secondary and tertiary flower aspect is 50°, moderate in strength, surface matte and densely covered with very short soft glandular hairs; average of 0.5 mm in length and to small to measure color.

Reproductive organs:

*Gynoecium.*—Pistils; 2, 3 mm in length, stigma; club-shaped, NN155A in color, 0.2 mm in diameter, style; an average of 2.75 mm in length and N155A in color, ovary; 150D in color.

*Androecium.*—Stamens; 5, anthers; triangular in shape, about 0.3 mm in length and width, 11C in color, filament; 2 mm in length and NN155D in color, pollen; low in quantity and 11D in color.

*Seed/fruit.*—No fruit or seeds were observed to date.

It is claimed:

1. A new and distinct cultivar of *Heuchera* plant named 'Maple Leaf' as herein illustrated and described.

* * * * *